United States Patent [19]

Gresham

[11] 3,944,633

[45] Mar. 16, 1976

[54] PHOSPHATE ESTERS

[75] Inventor: John T. Gresham, Somerset, N.J.

[73] Assignee: FMC Corporation, Philadelphia, Pa.

[22] Filed: Oct. 31, 1974

[21] Appl. No.: 519,434

Related U.S. Application Data

[62] Division of Ser. No. 422,841, Dec. 7, 1973, Pat. No. 3,883,478.

[52] U.S. Cl. .......................................... 260/927 R
[51] Int. Cl.² .......................................... C07F 9/15
[58] Field of Search ............................. 260/927 R

[56] References Cited
UNITED STATES PATENTS

| | | | |
|---|---|---|---|
| 3,801,677 | 4/1974 | Baranauckas et al. | 260/927 R X |
| 3,808,296 | 4/1974 | Brunetti | 260/927 R |
| 3,849,522 | 11/1974 | Hills | 260/927 R |

OTHER PUBLICATIONS

Derwent Japanese Patent Report, Vol. 5, No. 13, p. 5:5 (3-5-66).

*Primary Examiner*—Richard L. Raymond

[57] ABSTRACT

Flame-retardant polyester fibers containing 5 to 20% by weight of phosphate triester containing at least one mole of a hydroxymethyl bicyclic phosphate and 0–2 moles of a phenyl or naphthyl aryl compound as the sole flame-retardant additive or a two-component additive comprising the aforesaid triester in admixture with 20 to 80% of certain polychlorinated or polybrominated diaryl compounds.

4 Claims, No Drawings

PHOSPHATE ESTERS

This is a division of application Ser. No. 422,841, filed Dec. 7, 1973, now U.S. Pat. No. 3,883,478.

This invention relates to flame-retardant polyester fiber compositions. More particularly, this invention relates to flame-retardant polyester fibers which contain, as the flame-retardant additive, a complex phosphate triester.

Polyester compositions containing organic phosphorus and organic halogen compounds are known and are disclosed, for example, in U.S. Pat. No. 3,356,631 issued Dec. 5, 1971, to Jackson et. al.; U.S. Pat No. 3,645,962 issued Feb. 29, 1972, to Schwarz; U.S. Pat. No. 3,681,281 issued Aug. 1, 1972, to Juelke et al.; U.S. Pat. No. 3,688,001 issued Aug. 29, 1972, to Exner et al.; U.S. Pat. No. 3,708,328 issued Jan. 2, 1973, to Kelkheim et al., West German Pat. No. 2,001,125 (1970) to Caldwell et al. (Eastman Kodak Company), and U.S. Pat. No. 3,658,634 issued Apr. 25, 1972, to Yanagi et al. Bicyclic derivatives of phosphorus are known and are described, for example, in U.S. Pat. No. 3,293,327, issued Dec. 20, 1966 to Hechenbleikner et al and U.S. Pat. No 3,310,609, issued Mar. 21, 1967 to Baranauckas et al.

The various prior art flame-retardant polyester fiber compositions have a number of disadvantages in that they are either uneconomical for commercial use, or the additive is not compatible with molten polyester or is reactive with it, or the desired degree of flame retardancy is not obtained at suitable levels of concentration. It has always been desirable to provide efficient, but compatible flame-retardant additives which can be successfully incorporated into the molten polyester prior to the formation of fibers. Moreoever, a particular problem in the art has been successfully providing flame-retardant polyester fibers which, when blended with other fibers, retain their flame retardant characteristics and impart to the finished fiber blend a high degree of flame retardancy.

According to the present invention, there are provided flame-retardant polyester fiber compositions comprising from about 95 to 80 parts by weight of a fiber-forming linear polyester and 5 to 20, preferably 10 to 15, parts by weight of a phosphate triester flame-retardant additive having the formula

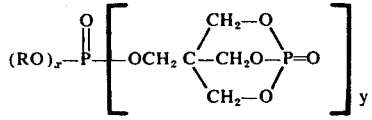

where R is an aryl radical selected from the group consisting of phenyl and naphthyl radicals and phenyl and naphthyl radicals containing one to three chlorine or bromine atoms and substituted derivatives of these radicals the substituents being methyl, methoxy, phenyl, phenoxy and phenyl and phenoxy containing one to five chlorine or bromine atoms, and $y$ is an integer from 1 to 3, preferably 1 or 2, and $x$ is $3 - y$. The latter described preferred embodiments, that is, those complex mixed phosphate triesters which contain one or two of the aforesaid aryl radicals are believed to be novel compounds and, as such, constitute a further embodiment of the present invention.

The complex phosphate triester flame-retardant additives of the present invention are readily prepared from the intermediate hydroxymethyl bicyclic phosphate, which is formed from pentaerythritol and triethyl phosphate in a two-step reaction as described in U.S. Pat. No. 3,293,327. The intermediate is then reacted with the appropriate phosphoryl chloride. Thus, reaction with $POCl_3$ will give a triester with 3 moles of the hydroxymethyl bicyclic phosphate, which is represented in the formula above when $y$ is 3. Reaction with compounds such as $ROP(O)Cl_2$ and $(RO)_2P(O)Cl$ will give mixed triesters represented by the above formula where $y$ is, respectively, 2 and 1, with R representing the desired aryl radical. Preferred are those novel mixed triesters wherein $x$ is 2 or 1 and R represents phenyl, naphthyl and mono-, di- or tri-bromophenyl or naphthyl radicals. Preferred embodiments are specifically exemplified by radicals such as 4-bromophenyl, 2,4-dibromophenyl, 1-bromo-2-naphthyl, 1,6-dibromo-2-naphthyl and 1,3,6-tribromo-2-naphthyl.

The phosphate triester flame-retardant additive of the present invention has a number of desirable properties, which render it particularly suitable for preparation of flame-retardant polyester fibers. It is soluble in molten polyester and does not adversely affect the physical properties of the finished polyester fiber. It is thermally stable at temperatures up to about 325°C and has a low volatility at 250°–300°C, the temperatures normally employed during the melt spinning of polyester fibers. Moreover, the additive of the present invention is substantially inert in the presence of molten polyester for extended periods of time, thus minimizing polymer degradation and crosslinking.

These properties enable the flame-retardant additive of the present invention to be incorporated into molten polyester prior to extrusion of the fiber. As is known in the art, polyester fibers are conventionally prepared by the melt spinning technique whereby molten polyester is extruded under pressure through a spinneret plate having a plurality of small circular openings about 0.009 inch in diameter. The spinning is carried out at a temperature of from about 260° to 300°C for poly(ethylene terephthalate) fibers. The polymeric polyester has been previously prepared either by the batch method or by the continuous polymerization technique.

Thus, a flame-retardant additive which is thermally stable, unreactive with and soluble in molten polyester and non-volatile at spinning temperatures is particularly advantageous in that no additional fiber processing steps are required to be added to the manufacturing sequence. The additive is simply blended with the polyester melt and fibers are prepared in the usual way.

Flame-retardant polyester fibers containing the aforesaid phosphate triester exhibit a high degree of flame retardancy. However, when polyesters are blended with other fibers, particularly cellulosic fibers such as rayon, the blended fiber usually exhibits an overall reduction in flame-retardant quality. Accordingly, a further embodiment of the present invention resides in flame-retardant polyester fibers comprising about 95 to 80 parts of a fiber-forming linear polyester and 5 to 20 parts by weight of a two-component flame-retardant additive consisting essentially of, by weight:

a. from about 20 to 80% of the aforesaid phosphate triester flame-retardant additive, and b. from about 80 to 20% of a polychlorinated or polybrominated diaryl compound containing at least 40% by weight chlorine or bromine and having the general formula:

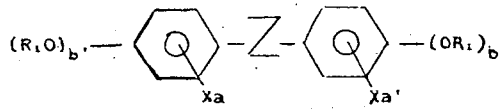

wherein X represents chlorine or bromine and $a$ and $a'$ are integers the sum of which is from 3 to 10; $b$ and $b'$ represent zero or 1; $R_1$ represents a member selected from the group consisting of $C_1$–$C_4$ alkyl radicals, $C_1$–$C_4$ acyl radicals such as acetyl, phenyl and benzoyl radicals and chlorinated and brominated phenyl and benzoyl radicals; Z represents a direct bond or a member selected from the group consisting of oxygen, carbonyldioxy, sulfonyl, $C_1$–$C_4$ alkylene, phenylene and chlorinated or brominated phenylene, dioxy radicals of the formula —$OR_2O$— where $R_2$ is $C_1$–$C_4$ alkylene, phenylene or chlorinated of brominated phenylene and ether linkages of the formula —$CH_2O$—, —$CH_2OCH_2$— and —$C_6H_4CH_2OCH_2C_6H_4$—.

Examples of suitable polychlorinated and/or polybrominated compounds may be shown by the following formulas I, II and III:

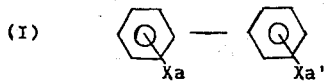

where X represents chlorine or bromine, $a$ and $a'$ are integers, the sum of which is from 3 to 10, preferably 5 to 10. Preferred compounds of this group include octabromobiphenyl, hexabromobiphenyl, decabromobiphenyl and the like;

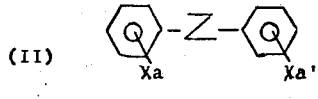

where X, $a$ and $a'$ are as previously described; Z may be oxygen, carbonyldioxy, sulfonyl, $C_1$–$C_4$ alkylene, phenylene, chlorinated or brominated phenylene, dioxy radicals of the formula —$OR_2O$— where $R_2$ is $C_1$–$C_4$ alkylene, phenylene or chlorinated or brominated phenylene, or ether linkages of the formula —$CH_2O$—, —$CH_2OCH_2$— and —$C_6H_4CH_2OCH_2C^6H_4$—. Particularly preferred compounds of this class include those wherein Z is oxygen as exemplified by the polybrominated diphenyl ethers such as decabromodiphenyl ether and hexabromodiphenyl ether or where Z is an ether linkage as described above; and

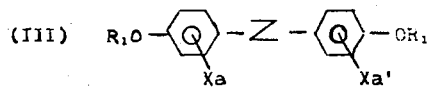

where X, $a$, $a'$ and Z are as described previously in formula II and $R_1$ represents $C_1$–$C_4$ alkyl, $C_1$–$C_4$ acyl radicals, phenyl and benzoyl radicals and chlorinated and brominated phenyl and benzoyl radicals. Preferred compounds of this class include tetrabromobisphenol A diacetate.

The polyesters which are rendered flame retardant in accordance with the present invention, include the fiber-forming linear saturated polyesters derived from saturated aliphatic and aromatic dicarboxylic acids and saturated diols.

These fiber-forming saturated polyesters are prepared from dicarboxylic acids such as terephthalic acid, isophthalic acid, adipic acid, bibenzoic acid, 4,4'-dicarboxyphenylmethane, 2,6-naphthalenedicarboxylic acid, 1,3-cyclopentanedicarboxylic acid, 1,3- or 1,4-cyclohexanedicarboxylic acid and the like. Diols generally employed to prepare the fiber-forming polyesters are the saturated aliphatic, saturated cycloaliphatic or aromatic diols, preferably the lower alkane diols such as ethylene glycol, propylene glycol, and butylene glycol. Other exemplary diols include ethylene diglycol, dimethylolcyclohexane, 1,6-hexanediol, p-xylylenediol and the like. Particularly preferred are fiber-forming polyesters such as poly (ethyleneterephthalate), poly (ethylene 2,6-naphthalenedicarboxylate) or poly (1,4-cyclohexylenedimethylene terephthalate) and blends of such polyesters. These fiber-forming polyesters generally have an average molecular weight of at least about 10,000.

Generally speaking, the total amount of two-component flame-retardant additive which is added to the polyester is from about 5 to 20% based on the combined weight of polyester and additive, that is, 5 to 20 parts by weight of additive and 95 to 80 parts by weight of polyester. These amounts provide the phosphorus, chlorine and bromine levels discussed below. The addition of amounts in excess of about 20% may interfere with the physical properties of the finished fiber as well as with the proper operation of the processing equipment, particularly the spinnerets used in extruding the fiber from the molten mixture of polyester and additive.

The relative amounts of phosphorus and chlorine or bromine present will, of course, be dependent on the degree of flame retardancy desired. In order to produce blends of polyester and cellulosic fibers which meet all existing standards for flame retardancy there should be present about 1 to 2% by weight of phosphorus in the fiber. At this phosphorus level, chlorine, if present, should be used in an amount such that the chlorine to phosphorus weight ratio is from 2:1 to 20: For the same level of phosphorus, that is, about 1 to 2%, the amount of bromine will be such that the weight ratio of bromine to phosphorus is between 2.5: and 10:1. Of course, chlorine and bromine both may be present and in such a case the chlorine to phosphorus weight ratio will be at the lower end of the aforesaid range, that is, about 2:1 to 10:1 and the bromine to phosphorus weight ratio will be about 2.5:1 to 5:1. In any event, the polyester fiber should not contain more than about 12% by weight of bromine as a maximum.

Polyester fibers of the present invention, which contain the aforesaid two-component flame-retardant additive, are particularly suitable for use in the preparation of blends of polyester with other fibers such as cotton, rayon, nylon, acetate, acrylics and the like. Particularly suitable are blends with cellulosic fibers such as rayon and acetate. Effectively rendering such blends flame retardant is a particular problem in the art, since under current standards the flame retardant qualities must be retained after repeated dry cleaning or laundering.

A particularly preferred embodiment resides in blends of 10 to 90 parts by weight, preferably 40 to 60 parts by weight, of a flame-retardant polyester fiber prepared in accordance with the present invention containing the aforesaid two-component flame-retardant additive with 90 to 10 parts by weight, preferably 60 to 40 parts by weight of flame-retardant regenerated cellulose filaments or fibers, as described in U.S. Pat. No. 3,455,713 issued July 15, 1969, to Godfrey. In brief, they are regenerated cellulose filaments having dispersed therein from 1 to 25% by weight of a substantially water-insoluble cyclical and/or linear liquid phosphonitrilic polymer having the general formula:

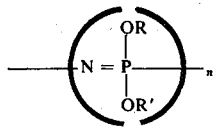

where R and R' are the same or different alkyl or alkenyl radicals having from one to six carbon atoms and $n$ is an integer of at least 3 and not more than about 20. These fibers are prepared by incorporating a flame-retardant amount of the phosphonitrilic polymer into filament-forming viscose, and spinning and regenerating the filament.

The invention is further illustrated by the following examples, which are not to be considered as limitative of its scope. All parts and percentages are by weight based on the total weight of the composition and temperatures are in degrees centigrade unless otherwise stated.

EXAMPLE 1

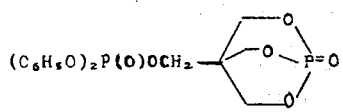

A slurry of 22.5 g (0.15 mole) of a hydroxymethyl bicyclic phosphate, 4-hydroxymethyl-1-oxo-2,6,7-trioxa-1-phosphabicyclo[2.2.2]octane, 10.1 g pyridine and 300 ml THF (tetrahydrofuran) was stirred and cooled to 15° in a nitrogen atmosphere. A solution of 34.6 g (0.125 mole) of 97% diphenyl chlorophosphate in THF was added slowly over 45 minutes. No exotherm was noticeable. After stirring and allowing the reaction mixture to warm to room temperature over a 1 hour period, the mixture was gradually heated overnight at 60°. Part of the solvent (200 ml) was removed by distillation. The reaction mixture was cooled to 10° and stirred as a precipitate formed. After about 10 minutes, 330 ml of ice water was added with stirring. The solids were collected by filtration and washed well two times with 300 ml of cold water. No chloride remained in the solid product. After drying 29.6 g (57% yield) of a white solid was obtained, mp 162°–163°.

The crystalline product was purified by recrystallization from reagent alcohol. White crystals were obtained, 27.4 g, mp 162°–164°.

| | | |
|---|---|---|
| Elemental Analyses: Calc'd for $C_{19}H_{16}O_8P_2$: | | % C, 49.53; |
| | | % H, 4.40; |
| | | % P, 15.02. |
| | Found: | % C, 49.17; |
| | | % H, 4.45; |
| | | % P, 15.09. |

EXAMPLE 2

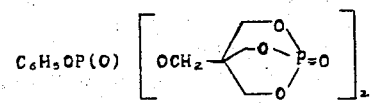

A slurry of 55.8 g (0.31 mole) of the hydroxymethyl bicyclic phosphate used in Example 1, 26.1 g of pyridine and 750 ml of THF was cooled under nitrogen to 15°. A solution of 32.7 g of phenyl dichlorophosphate in 150 ml of THF was added with good stirring over a period of 1 hour. No exotherm was apparent. The mixture was stirred and heated for 4 hours during which time it became homogeneous and then a precipitate began to form. After heating overnight at 50°, the solids were separated by filtration and washed four times with 400 ml of water. No chloride remained. A white powder was obtained after vacuum drying, 50.8 g (33% yield), mp 302°–305°.

The crude product was purified by soxhlet extraction using 1 liter of acetonitrile. After 5 hours, 90% had been extracted. After filtration, the liquid volume was reduced to 750 ml and allowed to cool in a refrigerator. The crystals that had formed were collected on a Buchner funnel and dried in vacuo, 43.5 g, mp 307°–309°.

| | | |
|---|---|---|
| Elemental Analyses: Cal'd. for $C_{16}H_{21}O_{10}P_3$: | | % C, 38.57; |
| | | % H, 4.25; |
| | | % P, 18.65. |
| | Found: | % C, 38.50; |
| | | % H, 4.46; |
| | | % P, 18.40. |

EXAMPLE 3

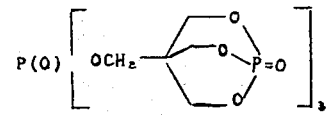

A slurry of 16.3 g (0.092 mole) of the hydroxymethylbicyclic phosphate used in Example 1, 7.75 g pyridine and 250 ml THF was stirred and heated to 35° under nitrogen. A solution of 4.8 g (0.031 mole) of phosphorus oxychloride in 25 ml of THF was added in 5 minutes. After heating at 35° for ½ hour the mixture was heated to 50° at which point the mixture became homogeneous and a viscous lower layer began to form. After heating overnight the thick lower layer was isolated by decanting the upper phase. The lower layer was mixed well with 150 ml of water. The solids were collected on a Buchner funnel and washed with several portions of water to remove chloride. After drying, 6.2 g (34% yield) of a white powder was obtained which did not melt or show signs of decomposition below 335°.

EXAMPLE 4

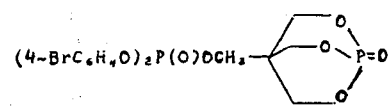

A mixture of 9.9 g (0.055 mole) of the hydroxymethyl bicyclic phosphate used in Example 1, 6.3 g (0.062 mole) triethylamine and 140 ml methylene chloride was stirred and cooled to 10°C. A solution of 25.6 g of bis(4-bromophenyl) chlorophosphate, mp 50°–55°, prepared by the method of E. N. Walsh, *J. Am. Chem. Soc.* 81, 3023 (1959)), in 40 ml methylene chloride was added over a 30-minute period, maintaining the temperature below 15°. After the addition the mixture was allowed to warm to room temperature, refluxed for 6 hours, and stirred overnight at room temperature. The reaction mixture was filtered and the filtrate washed with water, sodium bicarbonate and sodium carbonate solution. After drying with magnesium sulfate, the methylene chloride solution was concentrated to one-half its original volume and diluted at reflux with a threefold volume of carbon tetrachloride. On cooling the product crystallized and was isolated. A portion was decolorized with charcoal and recrystallized from reagent alcohol, mp. 149°–151°.

Elemental Analyses: Cal'd. for $C_{17}H_{16}Br_2O_8P_2$: % C, 35.81; % H, 2.83; % P, 10.87.
Found: % C, 35.58; % H, 2.94; % P, 10.75.

EXAMPLE 5

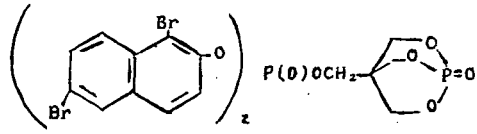

To a mixture of 18.0 g (0.1 mole) of the hydroxymethyl bicyclic phosphate used in Example 1, 10.5 g triethylamine and 450 ml of methylene chloride was added with stirring a solution of 15.4 g phosphorus oxychloride in 50 ml of methylene chloride. The reaction temperature rose to 33° during the 25 minute addition period. The mixture was heated at reflux for 6 hours and then allowed to stand at room temperature overnight.

A solution of 60.4 g 1,6-dibromo-2-naphthol, 21.0 g triethylamine, and 75 ml methylene chloride was added in 15 minutes at 15°. The mixture was slowly warmed to room temperature, heated at reflux for 6 hours and allowed to stand overnight at room temperature. 150 ml. of methylene 6 were removed by distillation. After cooling the solids were collected by filtration, dried and washed four times with water until no chloride was present in the washing. The solids were washed once with acetone and dried, 24.8 g, mp 310°–313°.

EXAMPLE 6

The Limiting Oxygen Index (LOI) of poly(ethylene terephthalate) plaques containing the phosphorus compounds of Examples 1–4 was determined to demonstrate the high degree of flame retardancy they imparted.

The plaques were prepared by grinding in a mortar mixtures of poly(ethylene terephthalate) and the flame retardant additive. On top of a 6 × 6 inch stainless steel plate one thirty-second inch thick) was placed a 6 × 6 inch Teflon coated aluminum plate and then a 6 × 6 inch brass frame one thirty-second inch thick with a 5¾ × 5¾ inch opening. Nine grams of the powdered mixture was spread evenly on the Teflon coated aluminum plate. A woven glass fabric (4⅝ × 5⅝ inch) weighing 3.9–4.1 grams was placed over the mixture inside the frame. An additional 9 grams of the mixture was spread evenly over the cloth and covered with an identical Teflon coated aluminum plate and a stainless steel plate. The mold assembly was placed in a hydraulic press previously heated to 275°C and the plates were closed gently at a slight pressure for 3 minutes to allow melting. The pressure was increased to 5 tons for 1 minute and then released. It was removed from the press, cooled between two large iron plates, and carefully taken apart to remove the glass fiber support plaque, which was cut into 3½ × 1¾ inch strips.

The LOI test is made by supporting the sample strip in a U-shaped frame which is mounted in a cylindrical open chamber. Controlled mixtures of oxygen and nitrogen gases are admitted into the base of the chamber and allowed to displace the normal atmosphere. When an equilibrium atmosphere in the chamber is obtained, the sample is ignited with a butane gas flame by contacting the flame with the top edge of the sample. If the sample fails to ignite, the oxygen ratio of the atmosphere is increased to a level where the flame will just propagate. Conversely, if the sample strip ignites and the flame propagates the oxygen ratio of the atmosphere is reduced to a level where flame propagation is virtually zero. The LOI is the minimum percentage concentration of the oxygen atmosphere in which the test sample will ignite and permit flame propagation. The LOI test wss introduced in 1966 (Fennimore et al., *Modern Plastics*, 43, 141 (1966) and is the basis for ASTM D-2863-70. The apparatus used was the Oxygen Index Flammability Tester Model JD14 manufactured by MKM Machine Tool Company, Inc. The results are given in the table below.

| Flame-Retardant Additive | % P | LOI |
|---|---|---|
| None | 0 | 21.5 |
| Ex. 1 | 2 | 27.5 |
| Ex. 2 | 2 | 28.0 |
| Ex. 3 | 2 | 28.8 |
| Ex. 4 | 2 | 29.2 |

EXAMPLE 7

The LOI of plaques containing poly(ethylene terephthalate), the phosphate triester of either Example 1 or Example 2 and varying amounts of decachlorobiphenyl, octabromobiphenyl and decabromodiphenyl ether was determined to demonstrate the high degree of flame retardancy imparted using the two-component flame-retardant additive of the present invention. The plaques were prepared as in Example 6 and contained sufficient phosphate triester and polyhalogenated compound to give the elemental concentration reported below:

| Sample No. | % P | % Halogen | LOI |
|---|---|---|---|
| 1 | 2% (Ex. 1) | 9.2% Cl[a] | 30.8 |
| 2 | 2% (Ex. 1) | 5% Br[b] | 30.8 |
| 3 | 2% (Ex. 1) | 5% Br[c] | 30.4 |
| 4 | 1% (Ex. 1) | 10% Br[c] | 32.4 |
| 5 | 2% (Ex. 2) | 5% Br[c] | 29.6 |

[a]decachlorobiphenyl was source of chlorine
[b]octabromobiphenyl was source of bromine
[c]decabromodiphenyl ether was source of bromine An LOI of about 30 is desirable for polyesters which are to be blended with cellulosic fibers.

EXAMPLE 8

A mixture of 20.1 g of the compound of Example 1 and 130.9 g of polyethylene terephthalate) having an intrinsic viscosity of 0.62 was spun from a laboratory apparatus at 280°C. Seventy-six grams of good white fiber was obtained. The intrinsic viscosity was 0.56 and tenacity was 3.75 g/den. Analysis of the fiber showed a phosphorus content of 1.98% by weight.

This poly(ethylene terephthalate) yarn was plied with a flame-retardant rayon containing about 15% by weight of a di-n-propyl phosphonitrilate (as described in U.S. Pat. No. 3,455,713) to give a 42%/58% blended yarn which was knitted into a 5.7 oz/sq. yd. fabric. The fabric passed the AATCC vertical flame test (34-1966). Five strips were conditioned at 65% relative humidity and ignited for 12 seconds with a butane gas flame with the following results:

| Sample | After Flame (sec) | Char Length (in) |
|---|---|---|
| 1 | 0 | 5.50 |
| 2 | 0 | 5.75 |
| 3 | 0 | 5.69 |
| 4 | 0 | 5.19 |
| 5 | 0 | 6.81 |

The vertical flame test is made by supporting a 3 × 10 inch fabric sample in a U-shaped frame which exposes 2 × 10 inch fabric. The sample and frame is supported vertically in a draft-free chamber with the open end of the fabric frame pointed down. Ignition of the fabric is made with a Tirrell Burner fueled with butane. A 1½ inch long frame is aligned to the based of the fabric so that ¾ inch of the flame bites into the fabric. Flame contact time is 12 seconds. Data are obtained to show the length of the char and the time of after flame. A sample passes the test if the average char length is 7 inches or less and no individual sample has a char length greater than 10 inches.

What is claimed is:

1. A compound of the formula

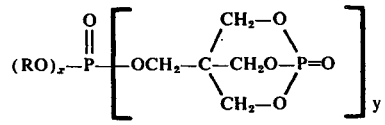

where R is an aryl radical selected from the group consisting of phenyl and naphthyl radicals and phenyl and naphthyl radicals containing one to three chlorine or bromine atoms and substituted derivatives of said radicals, the substituents being selected from the group consisting of methyl, methoxy, phenyl, phenoxy and phenyl and phenoxy containing 1 to 5 chlorine or bromine atoms and y is a integer, 1 to 1, and x is 3 − y.

2. The compound of claim 1 wherein R is selected from the group consisting of phenyl, naphthyl and phenyl and naphthyl containing one to three bromine atoms.

3. The compound of claim 2 wherein y is 1.

4. The compound of claim 3 wherein R is a member selected from the group consisting of 4-bromophenyl, 2,4-dibromophenyl, 1-bromo-2-naphthyl, 1,6-dibromo-2-naphthyl and 1,3,6-tribromo-2-naphthyl.

* * * * *

UNITED STATES PATENT OFFICE
CERTIFICATE OF CORRECTION

PATENT NO. : 3,944,633
DATED : March 16, 1976
INVENTOR(S) : John T. Gresham

It is certified that error appears in the above-identified patent and that said Letters Patent are hereby corrected as shown below:

Col. 3, line 49, "$C^6$" should read --$C_6$--.
Col. 4, line 44, "20:" should read --20:1.--.
Col. 5, line 41, "10.1" should read --10.0--;
line 62, in the Analyses, "$C_{19}H_{16}O_8P_2$" should read --$C_{19}H_{18}O_8P_2$--.
Col. 7, line 55, "methylene 6" should read --methylene chloride--.
Col. 9, line 16, "polyethylene terephthalate)" should read --poly(ethylene terephthalate)--.
Col. 10, line 31, "1 to 1" should read --1 or 2--.

Signed and Sealed this eighteenth Day of May 1976

[SEAL]

Attest:

RUTH C. MASON
Attesting Officer

C. MARSHALL DANN
Commissioner of Patents and Trademarks